US005741925A

United States Patent [19]
Mao et al.

[11] Patent Number: 5,741,925
[45] Date of Patent: Apr. 21, 1998

[54] TRANSVINYLATION OF NAPHTHENIC ACIDS

[75] Inventors: Chung-Ling Mao, Emmaus; Francis Joseph Waller, Allentown; Kenneth Merle Kem, Emmaus, all of Pa.

[73] Assignee: Air Products and Chemicals, Inc., Allentown, Pa.

[21] Appl. No.: 782,132

[22] Filed: Jan. 13, 1997

[51] Int. Cl.$^6$ .................................................. C07C 69/74
[52] U.S. Cl. .......................... 560/116; 560/118; 560/119; 560/120
[58] Field of Search ................................. 560/116, 117, 560/118, 119, 120

[56] References Cited

U.S. PATENT DOCUMENTS

| | | | |
|---|---|---|---|
| 4,981,973 | 1/1991 | Murray | 548/229 |
| 5,214,172 | 5/1993 | Waller | 554/165 |
| 5,223,621 | 6/1993 | Vallejos et al. | 554/165 |

FOREIGN PATENT DOCUMENTS 218149   4/1970   Russian Federation.

OTHER PUBLICATIONS

Ketterling, et al. *Applied Catalysis*, vol. 66 (1990), pp. 123–132.

*Primary Examiner*—Samuel Barts
*Attorney, Agent, or Firm*—Mary E. Bongiorno

[57] ABSTRACT

Vinyl naphthenate monomer mixtures are prepared by transvinylation of naphthenic acid in the presence of a catalyst of a palladium carboxylate complexed with one or more aryl N-containing ligands and distilling the resulting vinyl naphthenate monomers in the presence of the catalyst at pot temperatures exceeding 80° C. The catalyst is stable and can be re-used over several transvinylation reaction runs.

11 Claims, No Drawings

TRANSVINYLATION OF NAPHTHENIC ACIDS

BACKGROUND OF THE INVENTION

Naphthenic acid, a term commonly used in the petroleum industry, refers collectively to carboxylic acids in crude oil. Naphthenic acids are classified as monobasic carboxylic acids and can be represented by the general formula $C_nH_{2n-z}O_2$, where n indicates the carbon number and z specifies a homologous series; z=0 for saturated, acyclic acids; z=2 for monocyclic acids, z=4 for bicyclic acids; z=6 for tricyclic acids; and z=8 for tetracyclic acids. Some typical naphthenic acid structures are shown below:

vinyl naphthenates. Typically, therefore, naphthenic acid is first purified before reacting it with a vinyl ester. The following patent exemplifies this approach:

SU-218149 (1970) discloses a transesterification method for producing vinyl esters of lower aliphatic acids from naphthene carboxylic acids in the presence of catalytic amounts of mercury acetate and sulfuric acid. The naphthenic acid is purified and separated into individual $C_8$ to $C_{14}$ acids before transesterification. This transesterification method is problematic because mercuric acetate is a toxic material and sulfuric acid is very corrosive.

Other known methods for transvinylation are described below:

Ketterling, et al. (*Applied Catalysis*, Vol. 66 (1990), pages 123–132) disclose palladium acetate diimine complexes,

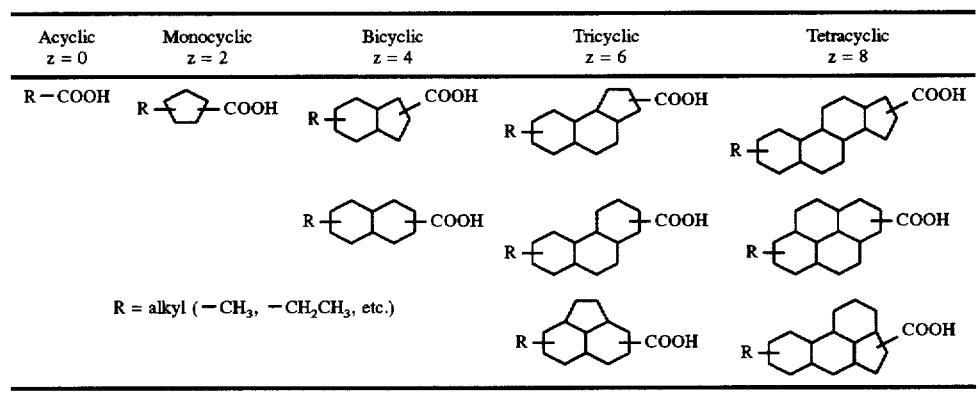

Commercial naphthenic acid contains impurities such as unsaponifiable hydrocarbons, phenolic compounds, sulfur compounds, and water. Naphthenic acid in the range of $C_7$ to $C_{20}$ is mainly monocyclic acids; however, separating a relatively pure cut of acids, such as a $C_{12}$ or $C_{18}$ fraction, from a broader cut is difficult and costly because of the low amounts of acids in petroleum crudes, the large amounts of fluid to be handled, and the large amounts of caustic-extractable compounds in most crudes. Distillation removes some of the phenolic and unsaponifiable impurities, but the distillation products of even highly refined naphthenic acid still contain significant levels of impurities; for example, commercial refined naphthenic acid contains from 1 to 20% impurities depending on the level of refinement. Composition and properties of several grades of commercial naphthenic acid are shown below:

COMMERCIAL NAPHTHENIC ACID

| Property | Crude | Refined | Highly Refined |
|---|---|---|---|
| Acid Nbr (mg KOH/g) | 150–200 | 220–260 | 225–310 |
| Acid Nbr (oil-free) | 170–230 | 225–270 | 230–315 |
| Unsaponifiables, wt % | 10–20 | 4–10 | 1–3 |
| Phenolic Cpds, wt % | 2–15 | 0.1–0.4 | 0.05–0.4 |
| Water, wt % | 0.3–1.0 | 0.01–0.1 | 0.01–0.08 |
| Spec.Grav. @ ° C. | 0.95–0.98 | 0.95–0.98 | 0.95–0.98 |
| Viscosity @ 40° C. (mPa) | 40–80 | 40–100 | 50–100 |
| Color, Gardner | black | 6–8 | 4–5 |
| Refr. Index, $n_D^{20}$ | 1.482 | 1.478 | 1.475 |
| Ave. MW (oil-free) | 240–330 | 210–250 | 180–250 |

One of the uses for naphthenic acid has been its conversion to vinyl esters. Although an inexpensive source of acids, especially cyclic monocarboxylic acids, the presence of even a small amount of impurities in naphthenic acid can cause problems in catalyst activity during the conversion to such as palladium acetate complexes with 2,2'-bipyridine and 1,10-phenanthroline, as catalysts for transvinylation of unsaturated and saturated carboxylic acids, such as acrylic and propionic acid.

U.S. Pat. No. 5,214,172 (Waller, 1993) discloses an improved process for transvinylation of a vinyl ester with either an alcohol or an acid, in which sulfur oxyacid or sulfur oxyacid mixture having a Hammett acidity ($-H_o$) of greater than 0.8 is added to a catalyst of palladium carboxylate complexed with one or more aryl N-containing ligands. The acid was found to be especially useful for improving the transvinylation of multi-basic acids such as adipic and glutaric acid.

U.S. Pat. No. 5,223,621 (Vallejos et al., 1993) discloses transvinylation of vinyl acetate or vinyl propionate and a carboxylic acid, such as benzoic and lauric acid, to form vinyl esters in the presence of a palladium catalyst that is made in situ. The catalyst is formed by reacting palladium (II) acetate, palladium (II) nitrate, palladium (II) hydroxide or palladium on charcoal with 2,2-bipyridyl, ortho-phenanthroline or tetramethylenediamine. The catalyst is precipitated and removed in the form of an oxalic acid complex or a chloride complex before distilling the vinyl ester product.

U.S. Pat. No. 4,981,973 (Murray, 1991) discloses the use of ruthenium-based catalysts in transvinylation reactions. Patentees teach, at col. 4, lines 47–56, that " . . . [u]nlike palladium, the ruthenium-based catalyst does not lead to observable metal precipitation, even when reaction is conducted at about 150° C. From a practical standpoint, the physical and chemical properties of the ruthenium catalyst (soluble, non-volatile, and possessing high thermal stability) permit product removal by distillation. These properties suggest that the ruthenium catalysts system is far superior to prior art transvinylation technologies using palladium and mercury."

BRIEF SUMMARY OF THE INVENTION

It was found in this invention that catalysts of palladium carboxylate complexed with one or more aryl N-containing ligands can be used effectively in the transvinylation of naphthenic acids and are stable at pot temperatures required to separate the products by distillation. Surprisingly, the catalysts are stable at pot temperatures above 80° C. which are required for distillation of the vinyl naphthenates product and the catalysts can be recycled over several uses. This procedure results in a very pure vinyl naphthenate monomer mixture (i.e., at least about 90% pure and frequently above 95% pure). The catalyst remaining in the pot can be recycled many times for use in subsequent transvinylation reactions without separation from the rest of the pot residue. Repeated use of the catalyst subjects it to pot temperatures well above 80° C. and concentrates the amount of impurities remaining with the catalyst, but there is little or no deactivation of the catalyst through several runs and no detectable deposit of palladium metal. The substantially pure vinyl naphthenate monomer mixture formed by this method can be used in emulsion polymerization reactions with other olefinically reactive monomers to form hydrophobic high molecular weight polymer latexes. Some of the advantages of this invention are listed below:

- it provides an improved and simple method of preparing vinyl naphthenates from naphthenic acid;
- the method employs a catalyst that can be re-used over several transvinylation reactions without separating it from impurities; and
- there is no detectable precipitation of palladium during the process.

BRIEF DESCRIPTION OF THE SEVERAL VIEWS OF THE DRAWINGS

Not Applicable.

DETAILED DESCRIPTION OF THE INVENTION

Naphthenic acid is classified as monobasic carboxylic acids of the general formula RCOOH, wherein R represents the naphthene moiety consisting primarily of alkyl-substituted cycloaliphatic groups, with smaller amounts of acyclic aliphatic groups. Naphthenic acid in the range of $C_7$ to $C_{20}$ consists mainly of saturated monocyclic and bicyclic adds. Aromatic, olefinic, hydroxy and dibasic acids are considered to be minor components. Commercial naphthenic acids contain varying amounts of impurities, such as unsaponifiable hydrocarbons, phenolic compounds, sulfur compounds and water, and are marketed by acid number, impurity level, and color. Merichem Company, one of the largest producers of naphthenic acids in the United States, sells the acids by grades; e.g., crude, semi-refined, refined and high purity grades. The high purity grades of naphthenic acid have an average molecular weight of about 180 g/mol to about 250 g/mol, and contain up to about 3% by weight of unsaponifiable impurities. Any grade of naphthenic acid can be used in this invention; however high purity naphthenic acid, containing up to about 3 wt % unsaponifiables and up to 0.4 wt % phenolic compounds, is preferred.

Transvinylation is the reaction of naphthenic acid with a vinyl ester, preferably vinyl acetate, in the presence of palladium carboxylate complexed with an aryl N-containing ligand. The reaction is carded out at atmospheric or elevated pressures. When vinyl acetate is used, the reaction temperature at atmospheric pressure is up to 72° C., the boiling point of vinyl acetate. Transvinylation reactions are typically conducted in the liquid phase but heterogenous and vapor phase systems can be used.

Catalysts used in transvinylation of naphthenic acid are palladium carboxylate complexes; preferably palladium acetate complexed with one or more aryl N-containing ligands. Examples of suitable aryl N-containing ligands include: 4,7-diphenyl-1,10-phenanthroline, 5-chloro-1,10-phenanthroline, 1,10-phenanthroline, 3,4,7,8-tetramethyl-1,10-phenanthroline, 2,9,4,7-tetramethyl-1,10-phenanthroline, 2,9-dimethyl-4,7-diphenyl-1,10-phenanthroline, 2,9-dimethyl-1,10-phenanthroline, 2,2'-dipyridyl, 4,4'-diphenyl-2,2'-dipyridyl, 4methyl-1,10-phenanthroline, 2,2'-biquinoline, 5-methyl-1,10-phenanthroline, isoquinoline, pyridine, and the like. The aryl N-containing ligand for the palladium catalyst can be part of a polymer support. Examples of suitable polymer supports are crosslinked polyvinylpyridines called Reillex® (available from Reilly Tar and Chemical Company.)

The aryl N-containing ligand complexes of palladium carboxylates can be prepared by the procedure described in U.S. Pat. No. 5,214,172. In general, palladium acetate complexes are insoluble in refluxing vinyl acetate. Once the mono-basic acids are added for transvinylation, the palladium acetate complexes become soluble. During this initial stage, the palladium acetate is anion exchanged to produce a palladium carboxylate. Alternatively, the aryl N-containing ligand palladium carboxylate can be made directly through combination of the palladium carboxylate and aryl N-containing ligand in a suitable solvent. The catalytic mechanism is not established, but the catalyst is defined, for purposes of this invention, in terms of the materials added to the reaction.

Transvinylation activity and purity of products can be determined using known IR and proton NMR techniques. IR techniques can be used to determine purity by measuring the absorbancy of the carbonyl group ($v_{c=o}$) in the organic acid and the absorbancy of the double bond ($v_{c=c}$) in the vinylic ester. The first order rate constant for transvinylation can be determined by plotting $\ln (1+C_{vinyl}/C_{acid})$ vs time. The necessary Beer-Lambert calibration curves (absorbance vs molar concentration) for the vinyl group (used vinyl acetate as model) and carboxyl group (used naphthenic acid as model) can be prepared using chloroform as solvent. The molar extinction coefficients are 2.0 $M^{-1}$ and 5.0 $M^{-1}$ for vinyl acetate and naphthenic acid, respectively, at concentrations below 1.5M vinyl acetate and 0.5M naphthenic acid. Proton NMR techniques can be used to determine the number of protons by signal integration. This information together with acid-base titration data can be used to determine the average molecular weight of the vinyl naphthenates.

The vinyl esters formed in the transvinylation reaction are separated from impurities and unreacted naphthenic acid by distillation. Distillation pot temperatures can exceed 80° C. depending on the vacuum during distillation, the molecular weight of the esters formed, and the purity of the naphthenic acid starting material. For example, for naphthenic vinyl esters formed from a highly refined naphthenic acid having an average molecular weight of about 217 g/mole, the boiling point is 80° to 85° C. at 0.05 mm Hg; and the pot temperature will reach at least about 90° C. during distillation.

The invention will be further clarified by a consideration of the following examples, which are intended to be purely exemplary of the use of the invention.

Example 1-3 show transvinylation of H6827 and H6822 naphthenic acid, supplied by Merichem Company, using a dipyridyl palladium acetate catalyst.

Example 4 shows the effect of p-toluenesulfonic acid co-catalyst on the transvinylation of H6822 naphthenic acid using a dipyridyl palladium acetate catalyst.

The dipyridyl palladium acetate catalysts used in the examples were prepared according to the following procedure. A one-necked 100 ml round bottom flask was charged with 50 ml acetonitrile, 0.94 g (4.19 mmol) palladium acetate, and 0.99 g (6.35 mmol) 2,2'-dipyridyl. The contents of the flask were stirred with a magnetic stirrer and within a few minutes the solution changed from a rust brown to a yellow suspension. The suspension was stirred overnight at room temperature. The contents were filtered and washed with pentane to remove any non-reacted 2,2'-dipyridyl. The isolated yellow solid weighed 1.55 g (4.08 mmol.)

Example 1

Transvinylation of Naphthenic Acid (H6827) using Dipyridyl Palladium Acetate Catalyst A three-necked 500 ml round bottom flask equipped with a reflux condenser, thermometer, and magnetic stirrer was charged with vinyl acetate, naphthenic acid (H6827) and heated to reflux. H6827, supplied by Merichem, contains naphthenic acid (RCOOH) having an average molecular weight of 217 g/mole and an average of 12.4 carbons in the R group which is primarily cyclopentane derivatives. Table 1 provides the amounts of vinyl acetate and naphthenic acid used. Dipyridyl palladium acetate (0.9 g; 2.37 mmol) was added at reflux. During ten hours of reflux, small samples were withdrawn to measure the disappearance of the acid and appearance of the vinyl esters. After ten hours, the reaction contents were cooled and the vinyl acetate was removed with a rotary evaporator. The remaining liquid was distilled under reduced pressure using a short-path distillation column. The distilled clear liquid was examined by quantitative IR to determine the amount of acid, and the pot residue containing the catalyst was recycled to the next transvinylation. Five consecutive transvinylation reactions are summarized in Table 1. Vinyl naphthenate distillation products from all of the runs were combined and distilled again. The vinyl naphthenates had a boiling point range of 80°–85° C. @ 0.05 mm Hg. Gas chromatography of the vinyl esters on a capillary column showed a broad poorly-resolved band of at least 50 components. The broad band indicates the presence of many different naphthenic vinyl esters, including isomers, within the average molecular weight of the starting material. IR and proton NMR were conducted on the samples and confirmed the presence and purity of the vinyl esters mixture. At least 90% pure vinyl naphthenates was achieved in each of the five transvinylation reactions. The impurity was identified as naphthenic acid.

TABLE 1

| | Transvinylation of Naphthenic Acid (NA) Using Dipyridyl Palladium Acetate Catalyst | | | | | | | |
|---|---|---|---|---|---|---|---|---|
| | Vinyl | | Recycled | Rx | Liquid after | Distillation | | |
| Run | Acetate (g) | NA (g) | Cat.(g)* | Time (hr) | Roto-Vac (g) | F-1 (g) | F-2 (g) | Pot (g) |
| 1 | 158.04 | 56.02 | — | 10 | 61.77 | 35.69 (95% purity) | 2.56 | 16.97 |
| 2 | 158.13 | 37.51 | 15.85 | 10 | ND | 39.0 (95% purity) | 6.0 | 10.51 |
| 3 | 159.63 | 46.29 | 10.33 | 10 | 65.98 | 45.3 (94% purity) | — | 13.08 |
| 4 | 159.68 | 44.55 | 12.89 | 6 | 53.85 | 22.6 (96% purity) | 4.85 | 16.81 |
| 5 | 153.73 | 46.97 | 16.59 | 6 | 67.73 | 42.91 (90% purity) | — | 17.05 |

*Transfer of pot material from one pot to another in each successive run resulted in some loss of recycled catalyst.
F-1 and F-2: vinyl naphthenate fractions.
Pot: liquid in the pot after distillation; contains catalyst, impurities, and unreacted naphthenic acid.

Example 2

The procedure of Example 1 was repeated and the catalyst was recycled 7 times. Results are presented in Table 2 below:

TABLE 2

| | Transvinylation of H6827 Naphthenic Acid (NA) using Dipyridyl Palladium Acetate Catalyst | | | | | | | |
|---|---|---|---|---|---|---|---|---|
| | Vinyl | | Recycled | Rx | Liquid After | Distillation | | |
| Run | acetate (g) | NA (g) | Catalyst (g) | Time (hr) | Roto-Vac (g) | F-1 (g) | F-2 (g) | Pot (g) |
| 1 | 158.31 | 58.2 | — | 10 | 48 | 40.2 (94.8% purity) | — | 12.44 |
| 2 | 159.34 | 44.23 | 12.22 | 10 | 65.25 | 43.6 (96.1% purity) | — | 14.53 |

TABLE 2-continued

Transvinylation of H6827 Naphthenic Acid (NA) using Dipyridyl Palladium Acetate Catalyst

| Run | Vinyl acetate (g) | NA (g) | Recycled Catalyst (g) | Rx Time (hr) | Liquid After Roto-Vac (g) | Distillation F-1 (g) | F-2 (g) | Pot (g) |
|---|---|---|---|---|---|---|---|---|
| 3 | 159.38 | 47.55 | 14.39 | 10 | — | 49.14 | — | 13.93 |
| 4 | 160.01 | 44.04 | 13.75 | 6 | 75.48 | 36.5 (92.2% purity) | — | 23.67 |
| 5 | 166.01 | 47.02 | 23.48 | 6 | 77.41 | 18.69 (94.3% purity) | 36.45 (90.9% purity) | 15.5 |
| 6 | 160.1 | 47.07 | 15.47 | 6 | 81.82 | 25.43 (100% purity) | — | 40.98 |
| 7 | 161.2 | 48.64 | 40.98 | 6 | 89.82 | 45.55 (100% purity) | — | 43.73 |
| 8 | 160.1 | 47.01 | 43.73 | 6 | 71.62 | 41.51 (100% purity) | — | 27.22 |
| Total | 1284.6 | 383.76 (1.77 mol) | | | 300.62 | | 36.45 337.07* (1.39 mol) 78.5% conversion | |

F-1 and F-2: distillation fractions at pot temperatures to 120° C..
Pot: catalyst, unreacted naphthenic acid, and impurities.
* Total of F-1 and F-2.

Example 3

The same procedure was followed as outlined in Example 1, except that H6822 naphthenic acid, from Merichem Company, was used. H6822 naphthenic acid has an average molecular weight of 254 g/mol and an average number of carbons in the R group (R—COOH) of 15.8. The catalyst was reused in three subsequent transvinylations, in addition to its use in the original reaction (summarized in Table 3.) The pot temperature was between 120° and 140° C. during distillation. These results show that the transvinylation catalyst is stable to pot temperatures up to 140° C.

TABLE 3

Transvinylation of H6822 Naphthenic Acid (NA) Using Dipyridyl Palladium Acetate Catalyst

| Run | Vinyl Acetate (g) | NA (g) | Recycled Catalyst (g) | Rx Time (hr) | F-1(a) (g) | F-2(b) (g) | Pot (g) |
|---|---|---|---|---|---|---|---|
| 1 | 164 | 58.1 | — | 4* | 3.51 | 13.9 | 72.9* |
| 2 | 160 | 30.2 | 72.9 | 4 | 4.9 | 28.9 | ND |
| 3 | 165 | 30.2 | ND | 4* | 0 | 14.8* | ND |
| 4 | 174 | 0 | ND | 4 | 0 | 13.5 | ND |
| Total | | 118.5 (0.47 mol) | | | 79.5(c) (0.28 mol) 59.6% conversion | | |

F-1 and F-2: distillation fractions.
*IR, after distillation, showed mostly vinyl naphthenates.
(a)Pot temperature reached 120° C. at vacuum of ~1 mm Hg; IR showed no NA.
(b)Pot temperature reached 140° C. at vacuum of 0.2-0.7 mm Hg; ; IR showed no NA.
(c)Total of F-1 and F-2.
ND: not determined.

Example 4
Effect of p-Toluenesulfonic Acid Co-Catalyst on Transvinylation of Naphthenic Acid Reillex-palladium acetate is a heterogeneous version of the homogeneous dipyridyl palladium acetate catalyst. Reillex resin is an organic polymer of vinyl pyridine crosslinked with divinyl benzene. Transvinylation of H6822 naphthenic acid was conducted at 4 and 12 wt % loading of palladium acetate on Reillex and the reaction product analyzed. The following mixture was refluxed at 72° C., using the procedure of Example 1.

| Component | Amount (g) |
|---|---|
| Vinyl acetate | 164 |
| Naphthenic acid (H6822, BW969) | 58 |
| Reillex-palladium acetate catalyst (4 or 12 wt %) | 4.3 |
| p-Toluenesulfonic acid-H$_2$O | 2.9 |

Samples were removed every 90 minutes and the vinyl acetate was evaporated under a stream of nitrogen. An 0.1 g sample of reaction mixture was diluted with 1.2 g of chloroform and analyzed using an IR technique. The reaction in which 4 wt % catalyst was used, was not complete (naphthenic acid present) after 18 hours. The reaction in which 12 wt % catalyst was used, was complete (no naphthenic acid present) in 7.5 hours. Analysis of distillation products using IR and NMR techniques revealed poor selectivity to vinyl naphthenates. Instead, an ethylidene dinaphthenate appeared to be the predominant product as determined by NMR analysis in which there was a doublet at 1.3 ppm and a broadened quartet at about 6.7 ppm. This example shows that an acid co-catalyst did not enhance the formation of vinyl naphthenates.

The examples show that vinyl naphthenates can be formed by reacting naphthenic acid with vinyl acetate in the presence of a palladium acetate chelate complex and then distilling the vinyl naphthenates product in the presence of the catalyst. The catalyst remains stable in the pot with impurities and unreacted naphthenic acid starting material and can be used in subsequent transvinylation reactions without purification. It is shown that impurities found in naphthenic acid do not inhibit the production of vinyl naphthenates and do not inhibit the subsequent use of the palladium carboxylate chelate catalyst in other transvinylation reactions. It is also shown that even at temperatures exceeding 100° C., the catalyst is stable, i.e., there is no detectable precipitation of palladium, and can be recycled.

Example 4 shows that the addition of an acid co-catalyst, that is known to be useful in the transvinylation of carboxylic acids, does not enhance the transvinylation of naphthenic acid.

Without being bound in theory, it is believed that the palladium catalysts of this invention are thermally stable at temperature above about 80° C. because the naphthene moieties provide protective groups to the catalyst and prevent degradation during the distillation operation.

The vinyl naphthenates of this invention can be reacted with one or more reactive olefinic compound to form hydrophobic polymers that are useful in the production of pressure sensitive adhesives or other applications in which water and moisture resistance and adhesion to low surface energy substrates is needed.

What is claimed is:

1. A process for producing a vinyl naphthenate monomer mixture from naphthenic acid of the following formula: RCOOH, wherein R is predominantly $C_7$ to $C_{20}$ substituted and unsubstituted cycloalkyl groups, comprising:

(a) reacting the naphthenic acid with a vinyl ester under appropriate reaction conditions in the presence of a catalyst comprising a palladium carboxylate complex having one or more aryl N-containing ligands to form the vinyl naphthenate monomer mixture; and (b) distilling the vinyl naphthenate monomer mixture in the presence of the catalyst at pot temperatures exceeding 80° C.

2. The process of claim 1 wherein R is $C_{10}$ to $C_{20}$.

3. The process of claim 2 wherein the catalyst is dipyridyl palladium acetate.

4. The process of claim 2 wherein the vinyl ester is vinyl acetate.

5. The process of claim 2 wherein the catalyst consists essentially of a palladium carboxylate complex having one or more aryl N-containing ligands.

6. The process of claim 2 wherein the catalyst is recycled to step (a).

7. A process for transvinylation between a vinyl ester and naphthenic acid having the formula: RCOOH, wherein R is predominantly $C_7$ to $C_{20}$ substituted and unsubstituted cycloalkyl groups, comprising:

(a) reacting the naphthenic acid with the vinyl ester under appropriate reaction conditions in the presence of a catalyst added as an aryl N-containing ligand complex of palladium acetate, to form a vinyl naphthenate monomer mixture; and (b) distilling the vinyl naphthenate monomer mixture in the presence of the catalyst at pot temperatures exceeding 80° C.

8. The process of claim 7 wherein R is $C_{10}$ to $C_{20}$.

9. The process of claim 8 wherein the catalyst is dipyridyl palladium acetate.

10. The process of claim 8 wherein the vinyl ester is vinyl acetate.

11. The process of claim 8 wherein the catalyst is recycled to step (a).

* * * * *

UNITED STATES PATENT AND TRADEMARK OFFICE
CERTIFICATE OF CORRECTION

PATENT NO. : 5,741,925
DATED : Apr. 21, 1998
INVENTOR(S) : Mao, et al.

It is certified that error appears in the above-indentified patent and that said Letters Patent is hereby corrected as shown below:

Claim 1, Column 9, line 25, delete "$C_z$" and in its place, insert, -- $C_7$ --.

Signed and Sealed this

Twenty-third Day of June, 1998

Attest:

BRUCE LEHMAN

Attesting Officer

Commissioner of Patents and Trademarks